United States Patent [19]

El-Nokaly et al.

[11] Patent Number: 5,843,407
[45] Date of Patent: Dec. 1, 1998

[54] NON-SWEATING LIPSTICKS

[75] Inventors: Magda El-Nokaly, Cincinnati; Michael Lee Vatter, Okeana, both of Ohio; David William Walling, Parkton; Neil Campbell Leatherbury, Baltimore, both of Md.; Cheryl Lynn Peterson, Cincinnati, Ohio

[73] Assignee: The Procter & Gamble Company, Cincinnati, Ohio

[21] Appl. No.: 638,686

[22] Filed: Apr. 26, 1996

Related U.S. Application Data

[63] Continuation of Ser. No. 317,449, Oct. 7, 1994, abandoned, which is a continuation-in-part of Ser. No. 138,665, Oct. 18, 1993, abandoned.

[51] Int. Cl.$^6$ .......................... A61K 7/027; A61K 7/025
[52] U.S. Cl. ................. 424/64; 424/63; 424/DIG. 5; 252/299.01
[58] Field of Search ............................ 424/64, 63, 401, 424/DIG. 5; 252/299.01

[56] References Cited

U.S. PATENT DOCUMENTS

| | | | |
|---|---|---|---|
| 3,479,429 | 11/1969 | Morshauser et al. | 424/63 |
| 4,083,956 | 4/1978 | Shelton | 424/66 |
| 4,767,625 | 8/1988 | Mitsuno | 424/95 |
| 4,937,069 | 6/1990 | Shin | 424/66 |
| 5,034,216 | 7/1991 | Barone | 424/63 |
| 5,310,547 | 5/1994 | Dunphy | 424/64 |
| 5,474,778 | 12/1995 | Ichikawa | 424/401 |

FOREIGN PATENT DOCUMENTS

| | | | |
|---|---|---|---|
| 0522624 | 1/1993 | European Pat. Off. . | |
| A0522624A1 | 1/1993 | European Pat. Off. | A61K 7/027 |
| 0534823B1 | 3/1993 | European Pat. Off. . | |
| A0549267A1 | 6/1993 | European Pat. Off. | A61K 7/027 |
| A0566442A1 | 10/1993 | European Pat. Off. | A61K 7/027 |
| A0602902A2 | 6/1994 | European Pat. Off. | C08L 81/02 |
| 61-236716 | 10/1986 | Japan | A61K 7/025 |
| A1233206 | 9/1989 | Japan | A61K 7/00 |
| A829112 | 5/1981 | U.S.S.R. | A61K 7/02 |
| WO94/06400 | 3/1994 | WIPO | A61K 7/00 |

OTHER PUBLICATIONS

Ham et al., "Lipstick Formula Variations and Lipstick Properties", *Cosmetics and Perfumery*, vol. 90, pp. 27, 28, 32–34 (1975).

Dweck, :The Sweating of Lipsticks, *Cosmetics & Toiletries*, vol. 96, pp. 29–32 (1981).

Matsuda et al., "Solid–liquid Separation Phenomenon on the Surface of an Oil, Wax and Pigments Mixture (I) A Binary Oil–Wax System", *Shikizai*, vol. 57 (3) pp. 1–13 (1984).

Material Data Safety Sheet, Rheox, Inc., pp. 5–7, 9–11, (1992).

*Primary Examiner*—Sally Gardner-Lane
*Attorney, Agent, or Firm*—John M. Howell; George W. Allen

[57] ABSTRACT

The present invention relates to lipstick compositions which comprise wax, emollient and a gelling agent wherein the inclusion of the gelling agent facilitates the retention of emollient oils particularly under high humidity and temperatures. Lipsticks of the present invention contain moisturizers which may be delivered to the lips in a non-polar/lipophilic medium in a thermodynamically stable way by using associated structures. A method of making the lipstick is also disclosed.

21 Claims, No Drawings

NON-SWEATING LIPSTICKS

This is a continuation of application Ser. No. 08/317,449, filed on Oct. 7, 1994, now abandoned, which is a continuation-in-part of application Ser. No. 08/138,665, filed on Oct. 18, 1993 also abandoned.

FIELD OF THE INVENTION

This invention relates to lipstick compositions comprising waxes, emollients and gelling agents exhibiting good oil retention. Said lipsticks provide good moisturization of the lips.

BACKGROUND OF THE INVENTION

Lipsticks are a complex mixture of solid, semi-solid and liquid lipids such as waxes and emollients. Waxes, which are low-melting organic mixtures of compounds of high molecular weight similar to fats and oils except not containing glycerides, are typically used in commercially available lipsticks to suspend or co-solubilize the oils present into a one phase solid structure.

Sweating, the excretion of oils on to the surface of a lipstick, is a common problem among such commercially available lipsticks. Sweating typically occurs due to the inferior oil-binding capacity of the wax network and/or to a high oil content causing supersaturation. When the temperature increases wherein interaction between the network and the oil changes, sweating occurs. Although this phenomenon can occur in any climate it is most likely to occur in sub-tropical and tropical climates.

Lipsticks compositions disclosed in PCT Patent Applications WO 94/06400, published Mar. 31, 1994 and WO 93/03887, published Nov. 25, 1993, incorporated herein by reference, contain emollients such as glycerine. These type of lipsticks are particularly prone to sweating since glycerine, which is hydroscopic, attracts water from the surrounding atmosphere wherein said water displaces the oils from the stick's matrix. This is particularly noticeable when such lipstick compositions are stored under high humidity and temperature conditions, i.e., greater than about 30° C. and about 70% relative humidity.

It has been discovered that adding gelling agents to the lipstick formula gels the emollient oils making said lipsticks sweat-resistant or sweat-free for significant periods of time at high temperatures and relative humidities. Generally, the lipsticks of the present invention are sweat-free for at least about 5 days and preferably at least about 10 days at about 90° F. (32° C.) and about 90% relative humidity. Further, the lipsticks of the present invention reabsorb the excreted oil upon removal from adverse conditions.

All percentages expressed herein are by weight percentage.

SUMMARY OF THE INVENTION

The present invention relates to lipstick compositions designed to deliver emollients to the lips while avoiding oil from collecting on the outer surface of said lipstick, particularly when said stick is subjected to high humidity. The lipstick compositions provide moisturizing, long wear and good feel properties. Said lipstick compositions comprise:
(a) from about 5% to about 90% wax;
(b) from about 1% to about 90% emollient selected from the group consisting of fats, oils, fatty alcohols, fatty acids ethers, fatty acid esters and mixtures thereof; and
(c) a sufficient amount of a gelling agent to avoid lipstick sweating wherein said lipstick composition has a rheology defined by a yield value from about 1.5 to about 3.0 grams-force, and a steady shear value from about 0.06 to about 0.25 grams-force per second.

The present invention also includes lipstick compositions as disclosed above additionally comprising association structures to additionally facilitate the delivery of said emollients to the lips. Said lipstick compositions containing surfactant association structures preferably have compatible solubilities for wax and oil components, can additionally comprise coupling agents, and are substantially free of castor oil.

DETAILED DESCRIPTION OF THE INVENTION

Definition

All components used herein are expressed as a percentage by weight of the composition.

As used herein, the term "solid material" refers to any solid lipstick ingredient capable of adsorbing the surfactant association structures. Solids include waxes, solid fats, waxy emulsifiers or pigments commonly used in lipsticks.

As used herein, "color(s)" includes pigments, dyes, colors, lakes, and pearl. Colors are measured on an anhydrous weight basis.

As used herein, the term "surfactant" refers to a low molecular weight or monomer non-polymeric organic compound amphiphilic in nature, i.e., it has hydrophilic and hydrophobic groups and exhibits a marked tendency to adsorb on a surface or interface and lower the surface tension. Surfactants or emulsifiers are divided into nonionic (no charge), anionic (negative charge), cationic (position charge) and amphoteric (both charges) based on whether or not they ionize in aqueous media. Surfactants are derived from natural oils and fats and crude oils. The term "surfactant" as used herein refers to mixtures of surfactants as well as a single organic compound.

As used herein, the term "lecithin" refers to a material which is a phosphatide. Naturally occurring or synthetic phosphatides can be used. Phosphatidylcholine or lechithin is a glycerine esterified with a choline ester of phosphoric acid and two fatty acids, usually a long chain saturated or unsaturated fatty acid, having 16–20 carbons and up to 4 double bonds. Other phosphatides capable of forming association structures, preferably lamellar or hexagonal liquid crystals, can be used in place of the lecithin or in combination with it. Other phosphatides are glycerol esters with two fatty acids as in the lechithin, but the choline is replaced by ethanolamine (a cephalin), or serine (α-aminopropanoic acid; phosphatidyl serine) or an inositol (phosphatidyl inositol).

As used herein, "solvent" means any polar or nonpolar material capable of forming an surfactant association structure with a surfactant. Some examples of polar solvents include glycerine, panthenol (preferably panthenol mixed with glycerine or alcohol), propylene glycol, butylene glycol, water, alcohols, alkanediols, polyethylene glycols, sorbitol, malitol and mixtures thereof.

Essential Components

A. Wax

The wax acts as a solidifying agent in the lipstick. It assists in the formation of the solid structure of the lipstick. The wax is comprised of organic compounds or mixtures of high molecular weight substances, and is solid at ambient temperature/room temperature. The wax can be hydrocarbons or esters of fatty acids and fatty alcohols. Waxes are thermoplastic. Natural, mineral and synthetic waxes can be used herein. As used herein "wax" refers to mixtures as well as a single type of wax.

Natural waxes can be of animal origin, e.g. beeswax, spermaceti, lanolin, shellac wax, of vegetable origin, e.g. ozokerite, ceresin, montan, paraffin, microcrystalline wax, petroleum and petrolatum wax. Synthetic waxes include polyol ether-esters such as carbowax and hydrocarbon-type waxes, silicone waxes and polyethylene wax. Generally, the waxes useful herein have melting points from about 55° C. to about 110° C. and are selected from the $C_8$ to $C_{50}$ hydrocarbon waxes.

The waxes useful in the present compositions are selected from the group consisting of candelilla, beeswax, carnauba, spermaceti, montan, ozokerite, ceresin, paraffin, modified beeswax, bayberry, castor waxes, synthetic waxes, microcrystalline waxes and mixtures thereof. More preferably the waxes are selected from the group consisting of microcrystalline, spermaceti, candelilla, modified beeswax, carnauba, ozokerite, paraffin, ceresin, and mixtures thereof. Most preferably, the waxes are selected from the group consisting of candelilla, ozokerite, paraffin, microcrystalline and mixtures thereof. A particularly preferred mixture of waxes used in the present invention comprises:
a. from about 3% to about 6% candelilla wax;
b. from about 2% to about 5% ozokerite wax;
c. from about 2% to about 5% paraffin wax; and
d. from about 1% to about 4% microcrystalline wax.

The amount of wax is used from about 5% to about 90%, preferably from about 10% to about 30% and most preferably from about 10% to about 20%, of the lipstick composition.

B. Emollient Component

The emollient component of the present invention aid application and adhesion, yield gloss and most importantly provide occlusive moisturization. As used herein, "emollient" means skin conditioning agents including emollients, humectants, occlusives, and other miscellaneous ingredients which condition the skin as disclosed in the C.T.F.A. Cosmetic Ingredient Handbook page 572, 1992. Said emollients include oils. Said emollient component typically comprises from about 5% to about 90%, preferably from about 25% to about 90%, and most preferably from about 70% to about 90% oils.

Oils are those materials which are organic substances that are liquid at ambient temperature. They are esters, triglycerides, hydrocarbons and silicones. These can be a single material or a mixture of one or more materials. The oils act as emollients and also impart desirable skin feel characteristics and viscosity to the lipstick. Suitable oils include caprylic triglycerides; capric triglycerides; isostearic triglycerides; adipic triglycerides; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hydroxystearate; octyl dodecanol; wheat germ oil; hydrogenated vegetable oils; petralatum; modified lanolins; branched-chain hydrocarbons; alcohols and esters; corn oil; cottonseed oil; olive oil; palm kernel oil; rapeseed oil; safflower oil; jojob oil; evening primrose oil; avocado oil; mineral oil; sheabutter; octypalmitate; maleated soybeam oil; glycerol trioctanoate; diisopropyl dimerate; volatile and non-volatile silicone oils including phenyl trimethicone; and mixtures thereof.

It has been discovered that the lipsticks of the present invention containing surfactant association structures can be used to deliver moisturizing agents in lipsticks which are substantially free of castor oil. The removal of castor oil from the lipstick compositions of the present invention containing surfactant association structures allows for the optimization of emollients; thus, providing fro a more consumer acceptable feel, such as less lackiness, and moisturizing benefits by utilizing more lubricious emollients. An added benefit to removing the castor oil is the removal of the castor oil odor. By substantially free of castor oil, it is meant that the lipstick comprises less than about 0.1%, preferably less than about 0.01% and most preferably less than about 0.001%, of castor oil.

The preferred oils for use herein are caprylic triglycerides, capric triglycerides, isostearic triglyceride, adipic triglyceride, phenyl trimethicone, lanolin oil, polybutene, isopropyl palmitate, isononyl isononanoate, isopropyl isostearate, cetyl ricinoleate, octyl dodecanol, oleyl alcohol, hydrogenated vegetable oils, modified lanolins octyl palmitate, lanolin oil, maleated soybean oil, cetyl ricinoleate, glyceryl trictanoate diisopropyl dimerate, syntheic lanolin derivatives and branched chain alcohols and mixtures thereof.

Preferably, the oils used are selected such that the majority (at least about 75%, preferably at least about 80% and most preferably at least about 99%) of the types of oils used have solubility parameters which do not differ by more than from about 0.3 to about 1, preferably from about 0.5 to about 0.8. For example, the more preferred oils for use are lanolin oil, octyl palmitate, isopropyl palmitate isononyl isononoate and mixtures thereof. Their respective solubility parameters are 7.3, 7.4 and 7.8. Thus, the solubility parameters do not differ by more than about 0.5. (Solubility parameters as reported in "Cosmetics & Toletries", Vol 103, October 1988, p64, incorporated herein by reference.) It is also preferred that the oils and waxes utilized have compatible solubilities.

The more preferred oils for use herein have a solubility parameter of from about 7.3 to about 7.8. Examples of more preferred oils for use herein are lanolin oil, octyl palmitate, isopropyl palmitate, isononyl isononanoate and mixtures thereof.

Preferably, the oils are minimized in the present invention due to their tendency to sweat. A preferred embodiment of the present invention utilizes a coupling agent when the compositions comprise greater than about 40% oil.

Suitable emollients for use are isostearic acid derivatives, isopropyl palmitate, surfactants, lanolin oil, diisopropyl dimerate, maleated soybean oil, octyl palmitate, isopropyl isostearate, octyl hydroxystearate, cetyl lactate, cetyl ricinoleate, tocopheryl acetate, acetylated lanolin alcohol, cetyl acetate, lecithin, phenyl trimethicone, glyceryl oleate, tocopheryl linoleate, wheat germ glycerides, arachidyl propionate, isopropyl palmitate, myristyl lactate, decyl oleate, propylene glycol ricinoleate, isopropyl lanolate, pentaerythrityl tetrasterate, neopentylglycol dicaprylate/dicaprate, hydrogenated coco-glycerides, isotridecyl isononanoate, isononyl isononanoate, myristal myristate, triisocetyl citrate, cetyl alcohol, octyl dodecanol, oleyl alcohol, panthenol, lanolin alcohol, linoleic acid, linolenic acid and mixtures thereof.

Excess polar and nonpolar solvents used to forming surfactant association structures, as disclosed below, can be used as emollients, particularly the polar solvents such as glycerine. Other preferred polar solvent emollients include pyrrolidone carboxylic acid, sodium lactate or lactic acid, urea collagen, α-hydroxy propylglyceryl ether α-hydroxy acids (e.g., ethylglycolic acid, leucic acid, mandelic acid, glycollic acid), glucosamines, and elastin fibers, D-panthenol, alklantoin and hyaluronic acid and chondroitin sulfate. Please note that some of these can be delivered with the association structures by dissolving into the polar liquid.

The emollients can comprise from about 1% to about 90%, preferably from about 10% to about 80%, more preferably from about 20% to about 70%, and most preferably from about 40% to about 60%, of the lipstick composition.

C. Gelling Agent

In the present invention, gelling agents are used to establish a network in the stick matrix which is responsible for retention of the oils in the lipstick matrix in the present invention. Suitable gelling agents for use are selected from the group consisting of hydrophobic silicas, hydrophobic clays with an effective amount of an activator, propylene carbonate, ethyl cellulose, n-acyl amino acid amides and n-acyl amino acid esters, and mixtures thereof. The preferred gelling agents for use are hydrophobic silicas, hydrophobic clays with an effective amount of an activator, and mixtures thereof. The gelling agent is used in an amount sufficient to retain the oils in the lipstick matrix, but, not so much as to change the desired rheology of the lipstick, thereby negatively effecting the desired spreadability and lip feel when applied to the lips.

The desired rheology is determined by utilizing a compression/force measuring equipment known in the art, such as an Instron. A small cylindrical probe (a solid probe having a 0.25 mm outside diameter) is rigidly attached to a load cell. Said probe is pushed downward by mechanical means into the sample at a point no closer than 0.3 mm from the edge of the sample at a speed of 2.0 inches per minute. A plurality of measurements are taken of the sample at points no closer than 0.2 mm from where a previous measurement was taken. The force required to penetrate into the sample is plotted on the Y axis of a graph while the corresponding time value is plotted on the X axis, yielding a force/time curve fro the sample. The extrapolated Y intercept (where time is zero) of the curve corresponds to the yield value of the sample, while the slope of the curve m, measured in force/time corresponds to a steady shear viscosity-like value for the sample. the lipsticks of the present invention have yield value from about 1.5 to about 3.0 grams-force, and a slope m value from about 0.06 to about 0.25 grams-force/sec. A more detailed discussion of this method is found in U.S. Pat. No. 4,455,333, Hong et al., issued Jun. 19, 1984; incorporated herein by reference.

In the present invention a sufficient levels of gelling agents used are typically from about 0.1% to about 20%, preferably from about 1.0% to about 10% and most preferably from about 2.0% to about 8% of the lipstick compositions.

1. Hydrophobic Silicas

The hydrophobic silicas that are used herein are a very fine colloidal silicon dioxide which has been derivatized to make it hydrophobic. Preferably, the particles have an average diameter of less than about 50 nonometers, and usually are in the range of from about 7 to about 40 nonometers. Most preferably the particles are in range of 7–30 nanometers. These particles have a surface area in the range of from about 50 to about 380 m²/g. The smaller particles are fumed silica. Spray drying can also be used to obtain hydrophobic silicas suitable for use herein.

Hydrophobic silicas are made from hydrophilic silica by chemically modifying the silanol groups (SiOH) on the surface, using halosilanes, alkoxysilanes, and siloxanes. The silanes contain an organic group, e.g. alkyl, cycloalkyl or aryl group. These materials form a chemical bond on the surface of the silicon dioxide with a carbon, i.e. a carbon-silicon bond is formed. The organic (organo0 groups are substituted on the silica on the outer edge of the particle. The organic group can be any hydrocarbyl group selected from the group of $C_1$ to $C_8$ alkyl, cycloalkyl and aryl groups. The preferred organo groups are methyl, ethyl, propyl, butyl, cyclohexyl, phenyl, benzyl and methylphenyl. Compositions such as

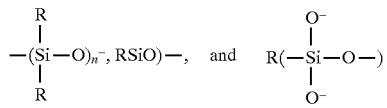

are all hydrophopic, R being a $C_1$ to $C_8$ alkyl, aryl or cycloalkyl group. Preferably R is methyl, ethyl or octyl and most preferably, R is methyl. Besides repelling water, hydrophobic silicas differ from the hydrophilic materials in having reduced water vapor absorption, and a reduced silanol group density. In general about 10% to 100% of the silanol groups are derivatized. Preferably at least 50% of the silanol groups are derivatized.

Suitable hydrophobic silicas are available from Degussa Corporation (Ridgefield Park, N.J.) under the trade names Aerosil. Preferred for use are Aerosil 200, Aerosil R972, Aerosil R974, Aerosil R8125, and Aerosil R202. Most preferred for use is the double treated Aerosil R812S. Other suitable hydrophobic silicas are produced by Cabot (Tuscola, Ill.) under the trade name Cab-O-Sil TS-530, TS--610 and TS-720. Preferred for use are Cab-O-Sil TS720 and TS530.

Hydrophobic silicas can comprise from about 0.1% to about 10%, preferably from about 2% to about 8% and most preferably from about 5% to about 7% of the lipstick compositions. Preferably, hydrophobic silicas are used in combination with hydrophobic clays with an effective amount of an activator, amino acid gelatinizing agents and mixtures thereof. More preferably, hydrophobic silicas are used in combination with bentonite clays and an effective amount of propylene carbonate as an activator.

Preferably when utilizing hydrophobic silicas in combination with other gelling agents, the ratio of hydrophobic silica to other gelling agent is about 1:1 or such that the volume of hydrophobic silica is equal to or greater than volume of the other gelling agents.

2. Hydrophobic Clays

Hydrophobic clays suitable for use are hydrophobically treated Hectorite and Bentonite clays. Many such hectorite clays are commercially available. They include for example, Bentone 38 sold by Rheox Corp. Such bentonite clays useful in the present invention include, for example, Bentone 27 and 38 sold by Rheox Corp.

The hectorite and bentonite clay minerals of the compositions can be described as expandable (swellable) three layer clays, in which a sheet of aluminum/oxygen atoms or magnesium/oxygen atoms lies between two layers of silicone/oxygen atoms, i.e., aluminosilicates and magnesium silicates, having an ion exchange capacity of at least about 50 meq/100 g. of clay, and preferably at least about 60 meq/100 g. of clay. The term "expandable" as used to describe clays relates to the ability of the layered clay structure to be swollen or expanded on contact with water. Such hectorite and bentonite clays are described in Grim, Clay Mineralogy (2nd. Ed) pp. 77–79 (1968), and in Van Olphen, An Introduction to Clay colloid Chemistry, (2nd Ed.) pp. 64–76 (1977), both of which are incorporated by reference herein.

The clay minerals employed in the compositions of the instant invention contain exchangeable cations including, but not limited to, protons, sodium ions, potassium ions, calcium ions, magnesium ions, lithium ions, and the like.

It is customary to distinguish between clays on the basis of one cation predominantly or exclusively absorbed. For example, a sodium clay is one in which the absorbed cation is predominantly sodium. As used herein, the term clay, such as a hectorite clay, includes all the various exchangeable cation variants of that clay, e.g., sodium hectorite, potassium hectorite, lithium hectorite, magnesium hectorite, calcium hectorite, etc.

The clay minerals employed in the compositions of the present invention are made hydrophobic by treating them with a cationic surfactant material. A preferred cationic surfactant is a quaternary ammonium cationic surfactant. A particularly preferred cationic surfactant is ditallow dimethyl ammonium chloride (e.g., quaternium-18).

Preferred clays for use are Bentone 27 and Bentone 38 from Rheox, Inc.

The compositions of this invention contain an effective amount of "activator" for the hectorite and bentonite clays that enables the hydrophobically-treated clays of this invention to gel the oils. Many such activators are known in the art, including for example, propylene carbonate, ethanol, and mixtures thereof. The preferred activator for use is propylene carbonate. Preferably, the ratio of clay to activator is about 3:1. Preferably the hydrophobic clays and activator are used in combination with other gelling agents, preferably with hydrophobic silicas, preferably at about a 1:1 ratio of clay to silica.

3. Propylene Carbonate

Propylene carbonate may be used as a gellant in the present invention. Propylene carbonate, as disclosed in the C.T.F.A. International Cosmetic Ingredient Dictionary, 1991 at page page 491, is available from a number of commercial sources as listed therein.

4. Ethyl Cellulose

Ethyl cellulose may be used as a gellant in the present invention. Ethyl cellulose, as disclosed in the C.T.F.A. International Cosmetic Ingredient Dictionary, 1991 at page page 196, is available from a number of commercial sources, including a preferred commercially available ethyl cellulose from Dow Chemical (Ethocel).

5. N-Acyl Amino Acid Derivatives

Gelling agents of the present invention include n-acyl amino acid amides and n-acyl amino acid esters as disclosed in PCT Application WO93/03887, published Nov. 25, 1993, herein incorporated by reference. These gelling agents, commonly referred to as GP-1, are prepared from glutamic acid, alanine, lysine, glutamine, aspartic acid and mixtures thereof. Preferred are the n-acyl glutamic acid amides and n-acyl glutamic acid esters having the structure:

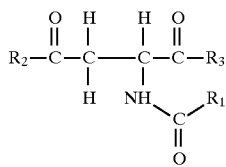

wherein:
(a) $R_1$ is alkyl, or aryl;
(b) $R_2$ and $R_3$ are, independently, alkyl, or aryl ester or amide; $R_2$ and $R_3$ are preferably the same.

Both d and l amino acids are effective in the subject invention; however, natural amino acids (l isomers) are preferred. Preferred secondary gellants include N-lauroylglutamic acid diethylamide, N-lauroylglutamic acid dibutylamide, N-lauroylglutamic acid dihexylamide, N-lauroylglutamic acid dioctylamide, N-lauroylglutamic acid didecylamide, N-lauroylglutamic acid didodecylamide, N-lauroylglutamic acid ditetradecylamide, N-lauroylglutamic acid dihexadecylamide, N-lauroylglutamic acid distearylamide, N-stearoylglutamic acid dibutylamide, N-stearoylglutamic acid dihexylamide, N-stearoylglutamic acid diheptylamide, N-stearoylglutamic acid dioctylamide, N-stearoylglutamic acid didecylamide, N-stearoylglutamic acid didodecylamide, N-stearoylglutamic acid ditetradecylamide, N-stearoylglutamic acid dihexadecylamide, N-stearoylglutamic acid distearylamide and mixtures thereof. Most preferred secondary gellants include n-lauroylglutamic acid dibutylamide, n-stearylglutamic acid dihexylamide, and mixtures thereof.

Surfactant Association Structures

Lipstick compositions of the present invention may additionally include from about 0.1% to about 80% of an surfactant association structure consisting essentially of:
(1) from about 3% to about 96%, by weight, of polar solvent; and
(2) from about 4% to about 97%, by weight, of surfactant having a Krafft point at or below about ambient temperature. Said surfactant association structures helps to thermodynamically bind the moisturizers/polar solvents (discontinuous phase) and deliver them in a predominately nonpolar lipophilic matrix (continuous phase) is by using surfactant association structures. Use of these structures can also provide a means of thermodynamically binding the moisturizers/polar solvents in such a way which will allow incorporation of high levels of the moisturizing agents while exhibiting overall excellent stability of the moiturizers/polar solvents and providing good feel properties.

It has been discovered that surfactant association structures consisting essentially of a surfacant or mixture of surfactants having a Krafft point at or below about ambient temperature (about 20° C.) and a moisturizer/polar solvent can thermodynamically bind the moisturizer/polar solvent and homogeneously absorb in the lipophilic matrix while providing good feel and a means of delivering the moisturizing agents to the lips. Thus, the preferred association structures of this invention can be used to deliver the moisturizers/polar solvents without syneresis, the separation of the hydrophilic materials.

As used herein "association structure" refers to reverse micelle and lyotropic liquid crystal structures which are formed by the mixture of a surfactant or mixture of surfactants and a polar solvent or mixture of polar solvents or actives soluble in polar solvents at ambient temperature. The liquid crystalline state is an intermediate state between the solid and liquid states. It is often called a mesomorphic state. The association structures of the present invention are thermodynamically stable. They are distinguishable from gels or emulsions which have the polar solvent separate when subjected to ultracentrafugation. Separation means that generally at least 50%, more often at least 80% and usually at least 99%, of the polar solvent separates upon ultracentrafugation.

In the literature, association structures are also referred to as anisotropic fluids or in the case of the cubic phase as isotropic fluids, a fourth state of matter, liquid crystals, aggregates, or mesophases. These terms are used interchangeably. Association structures or aggregates are generally disclosed in the reference *Lyotropic Liquid Crystals* Stig Friberg (Ed.), American Chemical Society, Washington, D.C., 1976, pp 13–27 which is herein incorporated by reference.

The preferred association structures of the present invention, are prepared by mixing a surfactant having a Krafft point at or below about ambient temperature with a sufficient amount of a polar solvent to form the desired association structure. Each surfactant has a temperature and concentration range in which the surfactant association structure will exist based on the surfactant's chemical structure, the type of solvent being used, and the presence of any impurities. The liquid crystalline phase flows under shear and is characterized by a viscosity that is significantly different from the viscosity of its isotropic solution phase. Rigid gels do not flow under shear like liquid crystals. Also, when viewed with a polarized light microscope, liquid crystals show identifiable birefringence, as, for example, planar lamellar birefringence, whereas when isotropic solutions and rigid gels are viewed under polarized light, both show dark fields. Exceptions to this method of detection can occur for example with the cubic phases which can not be dectected by a polarized light microscope but can be detected by x-ray diffraction. Other methods of detection commonly used by ones of ordinary skill in the art are given infra.

Adding a gel or emulsion of a surfactant with a polar solvent to a fat, oil, wax or other hydrophobic medium often leads to unacceptable results because the compositions are not thermodynamically stable and don't readily mix. emulsifying the oil/water and surfactant does not provide a thermodynamically stable system. The polar solvent would be expected to separate during storage or use and with changes in temperature. Adding the association structures of the present invention to the same system provides a system which is stable on storage because the surfactant association structure of the surfactant and polar solvent are thermodynamically stable and adsorb on the wax. The association structures can tolerate wide changes of temperatures, e.g. from ambient temperature to about 100° C. The polar solvent is bound within multilayers and does not separate, even when ultracentrifuged.

Micelles are polymolecular aggregates in solutions. Normal micelles predominate in surfactant solutions about the critical micelle concentration which occurs at the Drafft temperature. The lipophilic groups accumulate in the liquid-like inner part of the aggregates. The hydrophilic groups are directed out towards the water or reverse. "Inverted" micelles in a hydrocarbon environment have their polar groups piled up in the inner part of the micelles. These reverse micelles can aggregate to form spherical, elongated, cylindrical, filament (worm-like or fiber-like) structures or mixtures thereof which can network in the hydrocarbon environment. The term "reverse micelles", as used herein, refers to these aggregates of reversed micelles which are the spherical, elongated, cylindrical, or filament structures and/jor mixtures thereof. The spherical reversed micelles are liquid-like and as they become larger, i.e., elongated, they are gel-like.

One type of association structure, the liquid crystals, are a fourth state of matter. They exist between the boundaries of the solid phase and the isotropic liquid phase (i.e. an intermediate between the three dimensionally ordered crystalline state and the disordered dissolved state). In this state some of the molecular order characteristics of the solid phase are retained in the liquid state because of the molecular surfactant association structure and long range intermolecular interaction. The ability of some compounds to form a mesophase, typically referred to as liquid crystals, was observed nearly a century ago.

Thermotropic liquid crystals are obtained by heating solid crystals at a temperature above which they are no longer stable. Such termotropic liquid crystals are well known in our day-to-day life, and have multiple applications as they exhibit variations in color with temperature and/or a magnetic field and/or an electric field. They are formed by elongated molecules and are used in some cosmetics for their visible impact (viscualization of actives). Lyotropic liquid crystals result from the interaction of surfactant with a solvent over a particular range of concentration and temperature. Low molecular weight lyotropic liquid crystals, i.e. liquid crystals formed from a low molecular weight emulsifier or organic amphiphile (a compound having both a polar and a nonpolar group, as a soap, lecithins or long chain fatty acid monoglyceride), are known to encapsulate and act as a delivery vehicle for drugs, flavors, nutrients and other compounds.

The association structures of the present invention are:
a) Reverse Micelles:
(1) Reverse micelles are known in the art as spherical reverse micelles, elongated reverse micelles, bicontinuous phase or L2 phase; and
(2) Cylindrical reverse micelles or reverse connected rod-shaped, work-like or fiber-like liquid crystals also known in the art as networking reverse cylinders, connected cylindrical reverse micelle structures, or connected cylinders; and
b) Lyotropic Liquid Crystals:
(1) Reverse hexagonal liquid crystals also known in the art as Hexagonal II or F phase;
(2) Cubic liquid crystals also known in the art as viscous isotropic and $I_2$ phase; and
(3) Lamellar liquid crystals also known in the art as the Lα neat phase and D phase.

The surfactant association structure of the present invention is selected from the group consisting of reverse micelles, lyotropic liquid crystals and mixtures thereof.

Preferred association structures are the cylindrical reverse micelle, reverse hexagonal liquid crystals, lamellar liquid crystals and mixtures thereof. The most preferred association structures are lamellar liquid crystals, reverse hexagonal liquid crystals and mixtures thereof. The association structures can be in the following phases: two phase liquid crystals, one phase liquid crystals, reverse micelles/liquid crystalline phase or liquid crystalline/solvent phase. Preferably the liquid crystals are substantially one phase or two liquid crystalline phase, i.e., at least about 90%, more preferably about 98% and most preferably at least about 99%, of the surfactant association structure is in the form of the liquid crystal.

The preferred association structures can comprise from about 0.1% to about 80% of the lipstick composition. Preferably, the association structures comprise from about 3% to about 75%, more preferably from about 10% to about 65%, and most preferably from about 30% to about 60%, of the lipstick composition comprises the association structures.

Surfactants

Surfactants useful for making the preferred association structures, of the present invention are those which can form association structures, preferably lamellar liquid crystals or reverse hexagonal, at ambient temperature when mixed with a polar solvent. Ambient temperature/room temperature as used herein typically means about 20° C. Generally ambient temperature can range from about 18° C. to about 27° C., preferably from about 20° C. to about 25° C., depending on such variables as geographical location, i.e. sub-tropical vs. temperate regions. One of ordinary skill in the art is able to determine if association structures form at ambient temperatures.

The definition of Krafft point is well known in the art and one of ordinary skill in the art can determine a surfactant's Krafft point. In general terms, Krafft point is the melting point of the hydrocarbon chains of the surfactants. It can also be expressed as the temperature at which the solubility of an association colloid in water suddenly increases because critical micelle concentration is exceeded and micelles form. See Ekwall, P., "Composition, Properties and Structure of Liquid Crystalline Phases in Systems of Amphiphilic Compounds" *Advances in Liquid Crystals* Vol. I, Chapter I, p.81, incorporated herein by reference.

In preparing a sample combination of surfactant and polar solvent to demonstrate the ability to form association structures, the surfactant needs to be sufficiently soluble in the polar solvent such that an surfactant association structurecan form at ambient temperature. One of ordinary skill in the art is capable of determining compatible interactions.

Any surfactant which forms association structures at ambient temperature and is suitable for use in cosmetics is suitable for use herein. Surfactants suitable for use in cosmetics do not present dermatological or toxicological problems. Anionic surfactants, nonionic surfactants, cationic surfactants, amphoteric surfactants and mixtures thereof are suitable for use. Preferably anionic surfactants, nonionic surfactants, cationic surfactants, amphoteric surfactans and mixtures thereof having a Krafft point at or below about ambient temperature are use. More preferably, nonionic surfactants, cationic surfactants, amphoteric surfactants and mixtures thereof having a Krafft point at or below about ambient temperature are used.

Types of anionic surfactants suitable for use are soaps; sulfonates such as alkane sulfonates (e.g., branched sodium x-alkane sulfonate where x≠1) paraffin sulfonates, alkylbenzene sulfonates, a-olefin sulfonates, sulfosuccinates and sulfosuccinate esters (e.g., dioctylsodium and disodium laureth sulfosuccinate), isethionates, acylisethionates (e.g., sodium 2-lauroyloxyethane sulfonate), and sulfalkylamides of fatty acids, particularly N-acylmethylaurides; sulfates such as alkyl sulfates, ethoxylated alkyl sulfates, sulfated monoglycerides, sulfated alkanolamides, and sulfated oils and fats; carboxylates such as alkyl caboxylate having a carbon chain length above $C_{12}$, acylsarcosinates, sarcosinates (e.g., sodium lauryl sarcosinate), ethoxylated carboxylic acid sodium salts, carboxylic acids and salts (e.g. potassium oleate and potassium laurate), ether carboxylic acids; ethoxylated carboxylic acids and salts (e.g. sodium carboxymethyl alkyl ethoxylate; phosphoric acid esters and salts (e.g., lecithin); acylglutamates (e.g., disodium n-lauroyl glutamate) and mixtures thereof. It should be noted that the safest alkyl sulfates for use generally have a hydrocarbon chain lengths above $C_{12}$.

Types of nonionic surfactants suitable for use are polyoxyethylenes such as ethoxylated fatty alcohols, ethoxylated alcohols (e.g., octaoxyethelene glycol mono hexadecyl ether, $C_{16}E_8$ and $C_{12}E_8$), ethoxylated fatty acids, ethoxylated fatty amines, ethoxylated fatty amides, ethoxylated alkanolamides, and ethoxylated alkyl phenols; triesters of phosphoric acid (e.g., sodium dioleylphosphate); alkyl amido diethylamines; alkylamido propylbataines (e.g., cocoamido propylbetaine); amine oxide derivatives such as alkyl dimethylamine oxides, alkyl dihydroxyethylamine oxides, alkyl amidodimethylamine oxides and alkyl amidodihydroxyethylamine oxides; polyhydroxy derivatives such as polyhydric alcohol esters and ethers (e.g., sucrose monooleate, cetostearyl glucoside, β to $C_{16}$), mono, di- and polyglycerol ethers and polyglycerol esters (e.g., tetraglycerol monolaurate and monoglycerides, triglycerol monooleate (such as TS-T122 supplied by Grinsted), diglycerol monoleate (such as TST-T101 supplied by Grinsted), ethoxylated glycerides; monoglycerides such as monoolein and monolinolein; diglyceride fatty acids such as diglycerol monoisostearate (e.g., Cosmol 41 fractionated supplied by Nisshin Oil Mills, Ltd) and mixtures thereof.

Types of cationic surfactants suitable for use are aliphatic-aromatic quaternary ammonium halides; quaternary ammonium alkyl amido derivatives; alkyl amindopropyl-dimethylammonium lactate, alkylamidopropyl-dihydroxyethylammonium lactate; alkyl amidopropyl morpholinium lactate; quaternary ammonium lanolin salts; alkyl pyridinium halides; alkyl isoquinolinium halides; quaternary ammonium imidazolinium halides; bisquaternary ammonium derivatives; alkylbenzyl dimethylammonium salts such as stearalkylammonium chloride; alkylethylmorpholinium ethosulfates; tetra alkyl ammonium salts such as dimethyl distearyl quaternary ammonium chloride and bis isostearamideopropyl hydroxypropyl diammonium chloride (Schercoquat 2IAP from Scher Chemicals); heterocyclic ammonium salts; bis(triacetylammonium-acetyl)-diamines and mixtures thereof.

Types of amphoteric surfactants suitable for use are alkyl betains such as dodecyldimethylammonium acetate and oleylbetaine; alkanolamides such as monoalkanolamides and dialkanolamides; alkyl amido propylbetains; alkyl amidopropylhydroxysultaines; acylmonocarboxy hydroxyethyl glycinates; acyldicarbody hydroxyethyl glycinates; alkyl aminopropionates such as sodium laurimino dipropionate; alkyl iminodipropionates; amine oxides; acyl ethylenediamine betains; N-alkylamino acids such as sodium N-alkylamino acetate; N-lauroylglutamic acid cholesterol esters; alkyl imidazolines and mixtures thereof.

Preferred anionic surfactants for use are sulfosuccinate esthers, isethionates, sarcosinates, sodium lauryl sulfoacetate, phosphate esthers, alkyl carboxylates having a hydrocarbon chain length above $C_{12}$, acylglutamates and mixtures thereof.

Most preferred for use are nonionic surfactants. Examples of preferred nonionic surfactants are carbohydrate surfactants such as sucrose monoester and alkyl glucosides; polyglycerol esters such as tetraglycerol monolaurate PG-3 diisostearate, triglycerol monooleate, and diglycerol monooleata; monoglycerides; diglycerol esters such as PG-2 monoisostearate, PG-2 monooleate, and PG-2 dioleate; sorbitan esters and mixtures thereof.

Preferred surfactants for use are polyhydricalcohol esthers and ethers such as sucrose monooleate, alkylglucosides having a carbon chain length of from $C_{10}$ to $C_{16}$, β octyl glucofuranosides; polyglycerol esters such as tetraglycerol monooleate or laurate; monoglycerides such as monoolein; phosphatides such as lecithin, bis isostearamidopropyl hydroxypropyl diammonium chloride; sorbitan oleate; dipentaerythritol fatty acid ester; n-lauroyl glutamic acid ester; tetra glycerol monolaurate; and mixtures thereof.

A variety of lecithins can be used. American Lecithin Company (Danbury, Conn.) supplies a Nattermann Phospholipid, Phospholipon 80 and Phosal 75. All of these function well in this system. Other lecithins which can be used alone or in combination with these are: hydrogenated lecithin supplied by Nisshin Oil Mills, Ltd; Actiflo Series, Centrocap series, Central Ca, Cetnrol series, Centrolene, Centrolex, Centromix, Centrophase and Centrolphil Series from Central Soya (Ft. Wayne, Ind.); Alcolec and Alcolec 439-C from American Lecithin; Canasperse form Canada Packers, Lexin K and Natipide from American Lecithin; and L-Clearate, Clearate LV and Clearate WD from the W. A.

Cleary Co. Lecithins are supplied dissolved in ethanol, fatty acids, triglycerides and other solvents. They are usually mixtures of lecithins and range from 15% to 75% of the solution as supplied. The lecithins are also supplied as powders. The purity of the powder varies, but the lecithin can be from 60% to 90% of the powder on a weight basis. The weight of phosphatide as used herein is the weight of the lecithin and not of the carriers or impurities.

In order to form the appropriate type of association structure, the lecithin must be sufficiently soluble in the polar solvent such that a liquid crystalline state can be formed at the temperature conditions of product preparation. Additionally, the lecithin association structures should be of a type which has the capability to flow under application of shear, preferably lamellar, hexagonal II (revrse hexagonal) or mixtures thereof.

Both natural and synthetic lecithins can be used. Natural lecithins are derived from oilseeds such as sunflower seeds, soybeans, safflower seeds and cottonseed. The lecithins are separated from the oil during the refining process. Eggs are also a natural source of lecithin.

The phosphatide can be used at a level of from about 25% to about 95%, preferably from about 30% to about 85% and most preferably from about 40% to about 70%, of the association structure. Preferably a mixture of a phosphatide with other surfactants capable of forming associations structures is used. When such a mixture is used the phosphatide is preferably used at levels of from about 0.1% to about 30%, preferably from about 0.1% to about 5% and more preferably from about 0.1% to about 1% of the lipstick composition. Most preferably lecithin is not utilized as an surfactant association structure forming surfactant, i.e., essentially free of lecithin (>0.01%).

Typically when utilizing a phosphatide as the surfactant for forming an surfactant association structure at levels of less than about 30% of the association structure, reverse micelles, cylindrical reverse micelles, reverse connected rod-shaped liquid crystals, and mixtures of these association structures will be formed. Typically when utilizing a phosphatide at greater than about 30% of the association structure, the preferred lamellar (L2) phase association structures will be formed.

Typical Formulations Can Utilize the Following Surfactants:
Amphoteric Surfactants
• N-alkyl amino acids (e.g., sodium N-alkylaminoacetate)
Δ• N-lauroylglutamic acid cholesterol ester (e.g., Eldew CL-301 Ajinomoto)
Anionic Surfactants
• Acylglutamates (e.g., disodium N-lauroylglutamate)
Δ• Sarcosinates (e.g., sodium lauryl sarcosinate) Grace, Seppic)
• Tauratas (e.g., sodium lauyl taurate, sodium methyl cocoyl taurate)
Δ• Carboxylic acids and salts (e.g., potassium oleate, potassium laurate, potassium-10-undecenoate; potassium, 11-Styryl)-undecanoate
• Ethoxylate carboxylic salts (e.g., sodium carboxy methylalkyl ethoxylate)
• Ether carboxylic acids
Δ• Phosphoric acid esters and salts (e.g., lecithin) DEA-oleth-10 phosphate
• Acyl isethionates such as sodium 2-lauroyloxyethane sulfonate
• Alkane sulfonates (e.g., branched sodium x-alkane sulfonate (x≠1)
• Sulfosuccinates e.g. dioctyl sodium sulfosuccinate, disodium laureth sulfosuccinate (MacKanate El, McIntyre Group Ltx.)
• Sulfosuccinates (aerosols)
  Sodium dibutyl sulfosuccinate
  Sodium Di-2-pentyl sulfosuccinate
  Sodium Di-2-ethylbutyl sulfosuccinate
  Sodium Di hexyl sulfoscuccinate
  Sodium Di-2 ethylhexyl sulfosuccinate (AOT)
  Sodium Di-2-ethyldodecyl sulfosuccinate
  Sodium Di-2-ethyloctadecyl sulfoscuccinate
• Sulfuric acid esters, e.g., sodium 2-ethylhept-6-enyl sulfate, sodium 11-Heneicosyl sulfate, sodium 9-Heptadecyl sulfate
• Alkyl sulfates e.g., MEA alkyl sulfate such as MEA-lauryl sulfate Cationic Surfactants
• Alkyl Imidazolines such as alkyl hydroxyethyl imidazoline, stearyl hydroxyethyl imidazoline (supplier Akzo, Finetex and Hoechst)
• Ethoxylated Amines such as PEG-n alkylamine, PEG-n alkylamino propylamine, Poloxamine e.g., PEG-cocopolyamine, PEG-15 tallow amine
• Quaternaries: Alkylbenzyl dimethyl ammonium salts, betains, heterocyclic ammonium salts and tetra alkylammonium salts.
Alkylamines, dimethyl alkylamine, dihydroxyethyl alkylamine dioleate
• Alkylbenzyl dimethylammonium salts (e.g., stearalkyl ammonium chloride)
• Alkyl betaines (e.g., dodecyl dimethyl ammonio acetate, oleyl betaine)
Alkyl ethyl morpholinium Ethosulfate
• Tetra alkyl ammonium salts (e.g., dimethyl distearyl quaternary ammonium chloride (Witco))
Δ• Bis isostearamidopropyl hydroxy propyl diammonium chloride (Schercoquat 2IAP from Scher Chemicals)
• 1,8-Bis (decyldimethylammonio)-3,6 dioxaoctane ditosylate Nonionic Surfactants
• Ethoxylated glycerides
• monoglycerides such monoolein, monolinolein, monolaurin
Δ• diglyceride fatty acid (e.g., diglycerol monoisostearate Cosmol 41, fractionated, Nisshin Oil Mills Ltd.)
Δ• Polyglyceryl esters (e.g., triglycerol monooleate (Grinsteal TS-T122), diglycerol monooleate (Grindstead TST-T101)
Δ• Polyhydric alcohol esters and ethers (e.g., sucrose monooleate (Ryoto, Mitsubishi-Kasei Food Corp.), β octyl glucofuranoside esters, alkyl glucoside such $C_{10}$–$C_{16}$ (Henkel)
• Diesters of phosphoric acid (e.g., sodium dioleyl phosphate)
• Ethoxylated alcohols (e.g., $C_{16}E_8$ (octaoxyethylene, glycol mono hexadecyl ether) and $C_{12}E_8$)
• Alkylamido propyl betaine (e.g. cocoamide propyl betaine)
• Amide: (e.g., N-(doderanoylaminoethyl)-2-pyrrolidone)
• Amide oxide: e.g.,
  1,1 Dihydroperfluorooctyldimethylamine oxide
  Doderyldimethylamine oxide
  2-Hydroxydodecyldimethylamine oxide
  2-Hydroxydodecyl-bis (2-hydroxyethyl) amide oxide
  2-Hydroxy-4-oxahexadecyldimethylamine oxide
• Ethoxylated amides (e.g., PEG-n acylamide)
• Amnonio phosphates (e.g., didecanoyl lecithin)
• Amine (e.g., octylamine)
• Ammonio amides e.g., N-trimethylammoniodecanamidate
N-trimethylammoniododecanamidate
• Ammonio carboxylates e.g.,
  dodecyldimethylammonioacetate
  6-didodecylmethylammoniohexanoate
• Monoglycerides e.g.,
  1 dodecanoyl-glycerol monalaurin
  1–13-docosenoyl-glycerol monoerucin
• Phosphonic and phosphoric esters and amides e.g.,
  methyl-N-methyl-dodecylphosphonamidate
  dimethyl dodecylphosphonate
  dodecyl methyl methylphosphonate
  N,N-dimethyl dodecylphosphonic diamide
• Polyoxyethylene (C8) e.g.,
  pentaoxyethylene Glycol p-n-octylphenyl ether
  hexaoxyethylene Glycol p-n-octylphenyl ether
• Polyoxyethlene (C10) e.g.,
  pentaoxyethylene Glycol p-n-decylphenyl ether
  decyl Glyceryl ether, 4-oxatetradecan-1,2-diol
  nonaoxyethylene glycol p-n-decylphenyl ether
• Polyoxyethylene (C11) e.g.,
  Tetraoxyethylene glycol undecyl ether
• Polyoxyethylene (C12) e.g.,
  3,6,9,13-tetraoxapentacosan 1,11-diol
  3,6,10-trioradocosan-1,8-diol
  3,6,9,12,16-pentaoxaoctacosan 1,14-diol
  3,6,9,12,15-pentaoxanonacosan-1,17-diol
  3,7-dioxanonadecan-1,5-diol
  3,6,9,12,15,19-hexaoxahentriacontan-1,16-diol
  pentaoxyethylene glycol dodecyl ether
  monaoxyethylene glycol p-n-dodecylphenyl ether
• Polyoxyethylene (C14) e.g.,
  3,6,9,12,16-pentaoxaoctacosan-1,14-diol
  3,6,9,12,115,19-heraoxatriacontan-1,17-diol
• Sulfone diimines e.g.,
  decyl methyl sulfone diimine
• Sulfoxides e.g.,
  3-decyloxy-2-hydroxypropyl methyl sulfoxide
  4-decyloxy-3-hydroxybutyl methyl sulfoxide
• Sulfoximines e.g.,
  N-methyl dodecyl methyl sulfoximine
Δ More preferred for use Commercially available cationic surfactans suitable for use are: Hamposyl C (cocoyl sarcosine coconut acids) supplied by Hampshire Chem. Corp.; Arquat 2H-75 supplied by Akzo; Schercoquat 21AP supplied by Scher. Chem.; and Schercoquat DAS supplied by Scher Chem. Commercially available anionic surfactants suitable for use are: Crodafos N10 supplied by Croda and Dioctyl Sodium Sulfosuccinate supplied by American Cynamid. Commercially available nonionic surfactants suitable for use are: Diglycerol monoisostearate, Cosmol 41, Fractionated supplied by Nisshin; Dimodan DGMO and Triodan 20 supplied by Grindsted; Generaol 122 E-10 Ethoxylated Soya Sterol, Generol E-16 and Generol E-5 supplied by Henkel; Sucrose Monooleate supplied by Mitsubishi; and Tetraglycerol Laurate supplied by Lonza. The surfactans can be used at levels from about 4% to about 97%, preferably from about 5% to about 95%, more preferably from about 20% to about 90%, and most preferably from about 30% to about 70%, of the association structure.

Polar Solvents

The solvents suitable for use and useful for making the preferred association structures of the present invention include any polar solvent acceptable for human ingestion. Suitable polar solvents include: water, alcohols, such as ethanol, propyl alcohol, isopropyl alcohol, hexanol, and benzyl alcohol; poloys, such as propylene glycol, polypropylene glycol, butylene glycol, maltitol, sorbitol, and glycerine; panthenol dissolved in glycerine; flavor oils; and mixtures thereof. Mixtures of these solvents can also be used. Preferred polar solvents are glycerine, sorbitol, panthenol in glycerine, propylene glycol, butylene glycol, water and mixtures thereof. Most preferably, water added by itself, i.e. other than the water present in commercially supplied solvents, is not utilized. Thus, the most preferred lipstick compositions of the present invention are essentially free of water, i.e., they contain less than about 3% and preferably less than about 1% water. The most preferred polar solvents for use are glycerine, panthenol, propylene glycol, sorbitol, sorbitol butylene glycol and mixtures thereof.

Typically, the lipstick compositions will comprise from about 0.1% to about 60%, preferably from about 1% to about 30%, more preferably from about 6% to about 20% and most preferabtly from about 8% to about 18%, polar solvent. In the preferred association structures, polar solvents are used at levels of from about 3% to about 96%, preferably from about 5% to about 95%, more preferably from about 10% to about 80% and most preferably from about 30% to about 70%, of the association structure.

Preparation of the Surfactant Association Structure

Formation of the association structure, i.e., reverse micelles and/or liquid crystals and the concentration at which such association structures occur is dependent upon a variety of factors including the specific types of surfactant, solvent, temperature, solubility of the surfactant in the solvent, and concentration of the surfactant in the carrier. The purity of the surfactant affects the concentration level at which the association structures and particularly the preferred form of lamellar liquid crystal form.

The polar solvent and surfactant are mixed together. Formation of the association structure, particularly the preferred lamellar or hexagonal liquid crystalline state is accelerated by mechanical agitation. Mixing, can be performed either by hand (i.e., using hand utensils) or with mechanical equipment useful for home, institutional, or industrial lipstick preparation. Extruders which provide a shearing operation with mixing can be used.

Generally the association structures are formed at ambient temperature/room temperature. The processing temperature will depend somewhat on the properties of the polar solvent. However, during processing the association structures will be exposed to temperatures in the range of from about 10° C. to about 100° C., preferably from about 70° C. to about 90° C. If the temperatures affect the association structures, the association structures will reform once cooled to ambient temperature.

The one-phse liquid crystal is most preferred. It is preferred that a substantially two phase liquid crystal, one-phase liquid crystal or single phase liquid crystal component of (preferably at least 90%) by utilized.

Separation and thus detection of the surfactant association structure from excess liquid (solvent or solution) or solid generally may be achieved by ultracentrifugation. Ultracentrifugation should be conducted using sufficiently high centrifugal forces (preferably within the range of from about 20,000 rpm to about 60,000 rpm for from about one hour to about sixteen hours utilizing a Beckman L8-80 centrifuge equipped with a SW60Ti Rotor or by applying about 300,000 * g for about one hour) to induce the formation of observable phase boundaries over a period of time. Under these conditions a good separation of the individual phases is obtained. The volume of each phase is determined by calibration of the centrifuge tube and the volume fraction of the individual phase thus calculated.

Addition of the Surfactant Surfactant association structure Lipsticks

The surfactant surfactant association structure can be used in conventional lipstick formulating as a substitute for castor oil, other oils, and other lipstick ingredients. The association structures can be formed before addition or the polar solvent component and surfactant component of the surfactant association structure can be added independently and the association structures will form in situ. Preferably from 10% to 60%, preferably from about 20% to about 50%, of the oil or wax component is replaced with the stable liquid crystal. Generally lipstick formulations can be adjusted without undue experimentation.

The surfactant association structur should be well mixed with the solid component of the composition. It is preferable to prepare the association structures first, preferably liquid crystals or revers hexagonal liquid crystals and more preferably lamellar liquid crystals, and then mix the association structures with the waxes and oils in order to most effectively achieve a microscopic distribution of the surfactant association structure in the solid.

The surfactant association structures, preferably lamellar liquid crystals and/or reverse hexagonal liquid crystals, can be mixed with the waxes while they are molten and the mixture molded by conventional means. Preferably, the waxes and emollient component are melted at a temperature of from about 70° C. to about 95° C., preferably from about 83° C. to 90° C., and the surfactant association structure is added with stirring. The mixture is then poured into a mold at room temperature. The molding temperature can be varied to give a more uniform stick. Other conventional lipstick making processes can be used.

Method of Preparation

Conventional lipstick methods of preparation can be utilized to prepare the lipstick compositions of the present invention. The preferred method of preparation when utilizing hydrophobic silicas and clays, propylene carbonate, etheyl cellulose and mixtures thereof comprises the steps of:
1) adding the [thickening]/gelling agent to a mixture of the oil, any liquid emollients and color/pigments;
2) preparing the association structures by mixing the polar solvents and surfactants;
3) adding and mixing to the mixtures of (2) the waxes and any optional ingredients and heating the resulting mixture to about 85° C.;
4) heating and stirring the mixture of (1) until the oil is solubilized;
5) adding with stirring the mixture of (4) the mixture of (3) until a homogeneous mixture is acheived; and
6) molding accoarding to standard techniques the mixture of (5).

D. Optional Ingredients

Although hypoallergenic lipsticks can be made into the present invention where said lipsticks do not contain fragrances, flavor oils, lanolin, sunscreens, particularly PABA, or other sensitizers and irritants, the lipsticks of the present invention may additionally contain a number of the following ingredients as well as other ingredients not specifically disclosed hereinafter to achieve a desirable lipstick composition.

1. Color

The lipsticks can contain from 0% to about 35%, preferably from about 1% to about 20% and most preferably from about 5% to about 15%, of color, on an anhydrous pigment weight basis. These are usually aluminum, barium or calcium salts or lakes. Preferably, dyes are present at from about 0.1% to about 4% and pearls from 0% to about 20%. Colors which are dispersed in castor oil are not preferred for use.

Preferably, the lipstick compositions of the present invention are substantially free of castor oil such that the lipstick comprises less than about 0.1%, preferably less than about 0.01% and most preferably less than about 0.001% castor oil.

Pigments are typically dispersed in castor oil for the good dispersion of the pigments when incorporated into the lipstick, thus providing an even distribution of color. It has been discovered that excellent dispersion of the pigment can be achieved by utilizing the association structures, preferably lamellar liquid crystals, as a means of incorporating the color/pigments into the lipstick. A preferred method of incorporating dry pigments comprises the steps of:
(a) preparing a mixture consisting essentially of:
(1) a polar solvent; and
(2) a surfactant selected from the group consisting of amphoteric, cationic, anionic and nonionic surfactants having a Krafft point at or below about ambient temperature and mixtures thereof; and
(b) stirring said mixture until association structures form;
(c) adding and mixing dry pigments until homogenous mixture is achieved;
(d) milling said mixture until uniform particle size is achieved; and
(e) adding and mixing the mixture of (c) to the remaining lipstick ingredients until a homogenous mixture is obtained.

If the ingredients of the lipstick composition are being processed such that the association structures are being formed in situ, the preferred method of incorporating the dry pigments is to slurry them in one or more of the liquid emollient ingredients.

It should be noted that during processing of the surfactant association structure lipstick compositions, there is an improvement in the form of a noted decrease in the amount of separation of pigment particles during processing and molding.

Colors/pigments suitable for use herein are all inorganic and organic colors/pigments suitable for use in lipstick compositions.

Lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein.

Preferred lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors and pigments can also be included in the lipsticks, such as dyes and pearls, titanium oxides, Red 6, Red 21, Brown, Russet and Sienna dyes, chalk, talc, iron oxides and titanated micas.

2. Flavor

Flavor oils such as peppermint oil, orange oil, citrus oil, or wintergreen oil can be used along with an alcohol or glycerine. Flavor oils are usually mixed in a solvent such as ethanol to dilute the flavor. The flavor oils useful herein can be derived form natural sources or be synthetically prepared. Generally, flavor oils are mixtures of ketones, alcohols, fatty acids, esters and terpenes. The term "flavor oil" is generally recognized in the art to be a liquid which is derived from botanical sources, i.e. leaves, bark, or skin of fruits or vegetables, and which are usually insoluble in water. The level of flavor oil used can range for 0% to about 5%, preferably from 0% to about 1% of the lipstick composition.

3. Emulsifiers

Emulsifiers which do not form association structures at ambient temperature with the polar solvent utilized therein can also be used. The overall concentration of the emulsifier can be from 0% to about 20% of the formulation, preferably from 0% to about 15% and most preferably from about 1% to about 10%.

These emulsifiers are used as coupling agents which have an affinity for the hydrophilic (not the polar solvent) and hydrophobic phases of the lipsticks, yet do not form association structures at ambient temperature. Examples of suitable coupling agents are sorbitan oleate, sorbitan sesquioleate, PG-3 diisostearate, dipentaerythritol fatty acid ester, cholesteral 12 hydroxystearate, and mixtures thereof.

4. Skin Care Active Ingredients

Skin care active ingredients in both water soluble and water insoluble forms can be added to the lipstick. Said ingredients include fat soluble vitamins such as vitamin A and E, sunscreens and pharmaceutically active ingredients. These skin care active ingredients include zinc oxide, chamomile oil, ginko biloba extract; pyroglutamic acid, salts or esters; sodium hyaluronate; 2-hydroxyoctanoic acid; sulfur; salicyclic acid; carboxymethyl cysteine, and mixtures thereof. These will normally be present in amounts of less than about 2% by weight, and generally in the range of about 01% to about 1% by weight of the composition A preferred embodiment of the present invention comprises from about 0.1% to about 30%, preferably from about 8% to about 15%, polar solvent and form about 5% to about 20% surfactants. The surfactants are preferably a mixture wherein from about 50% to about 75% of the mixture is made up of surfactants which have a Krafft point of at or below about ambient temperature and form association structures at ambient temperature and from about 25% to about 50% of the mixture is made up of surfactants which are coupling agents. Another preferred mixture of surfactants which can from association structures and surfactants which act as coupling agent is lecithin, PG-3 diisosterate, sorbitan monoleate, cholesterol 12 hydroxystearate and dipentaerythritol fatty acid ester. Another preferred mixture is dipentaerythritol fatty acid ester, lecithin, and PG-3 diisosterate.

The following examples illustrate the invention but are not intended to be limiting thereof.

EXAMPLE I

A lipstick composition of the present invention, which is substantially free of castor oil, is prepared as follows:

| Ingredient | Amount (weight percent) |
|---|---|
| Waxes: | |
| Ozokerite | 3.20 |
| Paraffin | 2.90 |
| Candelilla Wax | 4.30 |
| BeSquare 175 (Modified Beeswax) | 2.75 |
| Polybutene H-1500 | 3.00 |
| Oils: | |
| Octyl Palmitate | 10.83 |
| Lanolin Oil | 7.50 |
| Isopropyl Palmitate | 10.00 |
| Maleated Soybean Oil | 2.00 |
| Gelling Agents | |
| Bentone 38 | 2.00 |
| Propylene Carbonate | 0.67 |
| Pigments: | |
| Diisopropyl Dimerate | 13.00 |
| Pigment | 13.00 |
| Surfactants/Emulsifiers: | |
| Lecithin (Centrolex F) | 0.70 |
| PG-3 Diisostearate | 3.50 |
| Dipentaerythritol Fatty Acid Ester[1] | 4.50 |
| Polar Solvents: | |
| Glycerine | 6.00 |
| Miscellaneous: | |
| Vitamin E Acetate | 0.05 |
| Propylparaben | 0.10 |
| Mica | 10.00 |
| Total | 100.00 |

[1]Cosmol 168AR supplied by Nisshin Oil Mills, LTD.

The pigment is slurried in the diisopropyl dimerate. Add and mix into the slurry the oils and the [thickening]/gelling agent (hydrophobic clay and activator). The mixture is heated to about 85° C. with stirring. The surfactants and polar solvents are mixed together to form the surfactant association structurephase. The surfactant association structuremixture and the remaining ingredients are added to the [thickening]/gelling agent mixture with constant stirring until a homogeneous mixture is achieved. Once uniform, the composition is poured into molds at room temperature.

EXAMPLE II

A lipstick composition of the present invention is prepared as follows:

| Ingredient | Amount (weight percent) |
|---|---|
| Wax | |
| Ozokerite | 5.45 |
| Candelilla Wax | 4.30 |
| Paraffin | 2.90 |
| Polybutene H-1500 | 3.00 |
| Oils | |
| Octyl Palmitate | 11.00 |
| lanolin Oil | 6.00 |
| Isopropyl Palmitate | 11.00 |
| Maleated Soybean Oil | 2.00 |
| Diisopropyl Dimerate | 9.66 |
| Gelling Agents | |
| Bentone 38 | 2.00 |
| Propylene Carbonate | 0.67 |
| Surfactants/Emulsifiers | |

-continued

| Ingredient | Amount (weight percent) |
|---|---|
| PG-3 diisostearate | 3.50 |
| Lecithin | 0.70 |
| Misc. | |
| Vitamin E Acetate | 0.05 |
| Propylparaben | 0.10 |
| Mica | 10.00 |
| Polar Solvent | |
| Glycerine | 6.00 |
| Pigment Slurry | |
| Pigment | 13.00 |
| Diisopropyl dimerate | 8.67 |
| Total | 100.00 |

The composition is prepared as in Example I.

EXAMPLE III

A lipstick composition of the present invention is prepared as follows:

| Ingredient | Amount (weight percent) |
|---|---|
| Oils: | |
| Octyl Palmitate | 13.50 |
| Lanolin Oil | 8.50 |
| Isononyl Isonanoate | 8.50 |
| Maleated Soybean Oil | 2.00 |
| Cetyl Ricinoleate | 4.00 |
| Diisopropyl Dimerate | 12.00 |
| Gelling Agents: | |
| Hydrophobic Clay (Bentone 27) | 4.70 |
| Propylene Carbonate | 1.60 |
| Pigment: | |
| Pigment | 12.00 |
| Surfactants | |
| Lecithin (Centrolex F) | .70 |
| PG-3 Diisosterate | 3.25 |
| Sorbitan Oleate | 2.70 |
| Cholesterol 12 Hydroxystearate | 2.00 |
| Dipentaerythritol Fatty Acid Ester | 4.00 |
| Polar Solvents/Moisturizers: | |
| Glycerine | 6.00 |
| Waxes: | |
| Ozokerite | 3.50 |
| Paraffin | 3.25 |
| Candelilla Wax | 4.65 |
| BeSquare 175 (Modified Beeswax) | 3.00 |
| Miscellaneous: | |
| Tocopherol Acetate | 0.10 |
| Propylparaben | 0.05 |
| Total | 100.00 |

The composition is prepared as in Example I.

EXAMPLE IV

A lipstick composition of the present invention is prepared as follows:

| Ingredient | Amount (weight percent) |
|---|---|
| Oils: | |
| Octyl Palmitate | 13.50 |
| Lanolin Oil | 8.50 |
| Isononyl Isonanoate | 8.50 |
| Maleated Soybean Oil | 2.00 |
| Cetyl Ricinoleate | 4.00 |
| Diisopropyl Dimerate | 12.00 |
| Gelling Agents: | |
| Hydrophobic Clay (Bentone 27) | 4.70 |
| Propylene Carbonate | 1.60 |
| Hydrophobic Silica (Aerosil R974) | 2.00 |
| Pigment: | |
| Pigment | 12.00 |
| Surfactants | |
| Lecithin (Centrolex F) | .70 |
| PG-3 Diisostearate | 3.95 |
| Cholesterol 12 Hydroxystearate | 2.00 |
| Dipentaerythritol Fatty Acid Ester | 4.00 |
| Polar Solvents/Moisturizers: | |
| Glycerine | 6.00 |
| Waxes: | |
| Ozokerite | 3.50 |
| Paraffin | 3.25 |
| Candelilla Wax | 4.65 |
| BeSquare 175 (Modified Beeswax) | 3.00 |
| Miscellaneous: | |
| Tocopherol Acetate | 0.10 |
| Propylparaben | 0.05 |
| Total | 100.00 |

The composition is prepared as in Example I.

EXAMPLE V

A lipstick composition of the present invention is prepared as follows:

| Ingredient | Amount (weight percent) |
|---|---|
| Oils: | |
| Octyl Palmitate | 13.50 |
| Lanolin Oil | 8.50 |
| Isononyl isononanoate | 8.50 |
| Maleated Soybean Oil | 2.00 |
| Cetyl Ricinoleate | 4.00 |
| Diisopropyl Dimerate | 12.00 |
| Gelling Agent: | |
| Hydrophobic Silica (Aerosil R812S) | 7.00 |
| Pigment: | |
| Pigment | 12.00 |
| Surfactants | |
| Lecithin (Centrolex F) | 0.70 |
| PG-3 Diisostearate | 3.25 |
| Cholesterol 12 Hydroxystearate | 2.00 |
| Dipentaerythritol Fatty Acid Ester | 4.00 |
| Polar Solvents/Moisturizers: | |
| Glycerine | 6.00 |
| Waxes: | |
| Ozokerite | 3.50 |
| Paraffin | 3.25 |

| Ingredient | Amount (weight percent) |
|---|---|
| Candelilla Wax | 4.65 |
| Besquare 175 (Modified Beeswax) | 3.00 |
| Miscellaneous: | |
| Tocopherol | 0.10 |
| Propylparaben | 0.05 |
| Total | 100.00 |

The composition is prepared as in Example I.

EXAMPLE VI

A lipstick composition of the present invention is prepared as follows:

| Ingredient | Amount (weight percent) |
|---|---|
| Oils: | |
| Octyl Palmitate | 13.50 |
| Lanolin Oil | 8.50 |
| Isopropyl Palmitate | 8.25 |
| Maleated Soybean Oil | 2.00 |
| Cetyl Ricinoleate | 4.00 |
| Diisopropyl Dimerate | 12.00 |
| Gelling Agent: | |
| Hydrophobic Silica (Aerosil R974) | 5.00 |
| Pigment: | |
| Pigment | 12.00 |
| Surfactants | |
| Lecithin (Centrolex F) | 0.70 |
| PG-3 Diisostearate | 3.25 |
| Sorbitan Olealte | 5.00 |
| Cholesterol 12 Hydroxystearate | 2.00 |
| Polar Solvents/Moisturizers: | |
| Glycerine | 9.00 |
| Panthenol | 0.25 |
| Waxes: | |
| Ozokerite | 3.50 |
| Paraffin | 3.25 |
| Candelilla Wax | 4.65 |
| BeSquare 175 (Modified Beeswax) | 3.00 |
| Miscellaneous: | |
| Tocopherol | 0.05 |
| Propylparaben | 0.10 |
| Total | 100.00 |

The composition is prepared as in Example I.

EXAMPLE VII

A lipstick composition of the present invention is prepared as follows:

| Ingredient | Amount (weight percent) |
|---|---|
| Oils: | |
| Octyl Palmitate | 13.50 |
| Lanolin Oil | 8.50 |
| Isopropyl Palmitate | 8.50 |
| Maleated Soybean Oil | 2.00 |
| Cetyl Ricinoleate | 4.00 |
| Diisopropyl Dimerate | 12.00 |
| Gelling Agent: | |
| N-Lauroyl-L-glutamic acid-di-n-butyl amide[1] | 2.00 |
| Pigment: | |
| Pigment | 12.00 |
| Surfactants | |
| Lecithin (Centrolex F) | 0.70 |
| PG-3 Diisostearate | 3.25 |
| Sorbitan Olealte | 5.00 |
| Cholesterol 12 Hydroxystearate | 2.00 |
| Dipentaerythritol Fatty Acid Ester | 2.00 |
| Moisturizers: | |
| Glycerine | 9.00 |
| Panthenol | 1.00 |
| Waxes: | |
| Ozokerite | 3.50 |
| Paraffin | 3.25 |
| Candelilla Wax | 4.65 |
| BeSquare 175 (Modified Beeswax) | 3.00 |
| Miscellaneous: | |
| Tocopherol | 0.10 |
| Propylparaben | 0.05 |
| Total | 100.00 |

[1] GP-1 ® supplied by Ajinomoto, Inc.

The composition is prepared as in Example I.

EXAMPLE VIII

A lipstick composition of the present invention is prepared as follows:

| Ingredient | Amount (weight percent) |
|---|---|
| Oils: | |
| Octyl Palmitate | 13.50 |
| Lanolin Oil | 8.50 |
| Isopropyl Palmitate | 8.50 |
| Maleated Soybean Oil | 2.00 |
| Cetyl Ricinoleate | 4.00 |
| Diisopropyl Dimerate | 12.00 |
| Gelling Agent: | |
| N-Lauroyl-L-glutamic acid-di-n-butyl amide[1] | 2.00 |
| Pigment: | |
| Pigment | 12.00 |
| Surfactants | |
| Lecithin (Centrolex F) | 0.70 |
| PG-3 Diisostearate | 3.25 |
| Sorbitan Olealte | 5.00 |
| Cholesterol 12 Hydroxystearate | 2.00 |
| Dipentaerythritol Fatty Acid Ester | 2.00 |
| Moisturizers: | |
| Glycerine | 9.00 |
| Panthenol | 1.00 |
| Waxes: | |
| Ozokerite | 3.50 |
| Paraffin | 3.25 |
| Candelilla Wax | 4.65 |

-continued

| Ingredient | Amount (weight percent) |
| --- | --- |
| BeSquare 175 (Modified Beeswax) | 3.00 |
| Miscellaneous: | |
| Tocopherol | 0.10 |
| Propylparaben | 0.05 |
| Total | 100.00 |

[1])GP-1 ® supplied by Ajinomoto, Inc.

The composition is prepared as in Example I.

These compositions are useful as moisturizing lipsticks and are sweat resistant or sweat-free for significant periods of time at high temperatures and relative humidities. Generally, the lipsticks are sweat-free for at least about 5 days, preferably at least about 10 days, at about 90° F. (32.2° C.) and about 90% relative humidity.

Identification of Association Structures

Those skilled in the area of association structures will be able to identify association structures based upon known identification techniques.

In identifying association structures, it is preferred that the individual selected surfactants be combined with glycerine or water over a concentration range at about ambient temperature to determine if the individual selected surfactants are capable of forming association structures. When combined, surfactants and polar solvents will not form in the product if the selected surfactants do not form association structures at some concentration with glycerine or water at about ambient temperature. Well known identification techniques can be used on the mixture of the individual selected surfactants and glycerine or water.

Surfactant association structureformation for any particular surfactant and solvent combination is readily identified using one or more of several well known identification techniques. The onset of surfactant association structureformation an din particular the occurrence of the most preferred substantially one-phase liquid crystal state for a particular phosphatide or surfactant and solvent system can be identified by: (1) visual observation with the naked eye, (2) birefringent optical activity observed by light microscopy; (3) measurement of the phosphatide or surfactant/solvent system using NMR spectra; (4) x-ray diffraction; (5) presence of a characteristic "texture" pattern observable under polarized light microscopy; and/or (6) texture observed in freeze fractured micrographs by transmission electron microscopy (TEM). Typically, polarized light microscopy determination requires confirmation by one of the other above mentioned methods. Light microscopy of liquid crystals is described generally in The Microscopy of Liquid Crystals, Norman, Hartshorn, London, England and Chicago, Ill., U.S.A., 1974, which discusses birefringence of mesomorphic states and methods for microscopic observation and evaluation (Chapter 1, pp. 1–20). Birefringence is a preferred method for determining the occurrence of a liquid crystal.

The identification of association structures within the lipstick product is generally more difficult due to the presence of other compounds such as wax crystals or pigments. Thus, the preferred way for identification of association structures such as liquid crystals is to ultracentrifuge the lipstick sample as previously described, separate the layers, identify the layer with typical surfactant association structurebirefringence and submit that layer to testing by x-ray diffraction and/or transmission election microscopy (TEM). Freeze-fracture transmission electron microscopy (FF/TEM) is the more preferred method of identification. Most preferrably, FF/TE is utilized to confirm association structures which have been indicated by other well-known methods such as x-ray diffraction or NMR.

A preferred method for determining the occurrence of the association structures of the present invention is by transmission election microscopy (TEM). More preferably, the association structures are imaged by a freeze-fracture transmission electron microscopy (FF/TEM) method. The method is carried out as follows:

1. The outside cavity of a freezing container is filled with liquid nitrogen and the inner dewar of the freezing container is filled with liquid ethane (normal melting temperature of −172° C.). The ethane is allowed to freeze.
2. A small piece (1 mm×2 mm) is cut from the lipstick with a clean razor blade and placed in the well of a copper specimen holder.
3. Most of the frozen ethane in the dewar is melted by inserting a metal heat sink into the dewar.
4. Immediately after melting the ethane, the specimen holder containing the lipstick sample is picked up using a pair of tweezers and rapidly plunged into the liquid ethane.
5. After a few seconds, the specimen holder is removed from the ethane, quickly touched to the tip of a camel's hair brush to remove excess ethane, and immediately immersed in the liquid nitrogen to keep the sample cold.
6. The sample is transferred under liquid nitrogen to a JEOL JFD-9000C sample holder and then transferred into the chamber of a JEOL JFD-9000C freeze fracture unit. The temperature of the specimen stage in the unit should be about −175° C. Vacuum should be at least $5 \times 10^{-7}$ torr.
7. A knife inside the unit is cooled to a temperature of about −165° C.
8. The sample is fractured in the JEOL chamber using the pre-cooled knife.
9. Platinum-carbon is deposited onto the fractured sample at a 45° angle for 4.5 seconds, followed by carbon deposition at a 90° angle for 25 seconds to form a replica of the fractured sample. The high voltage is 2500 V and the current is 70 mA.
10. The samples are removed from the freeze-fracture unit and cleaned in subsequent solutions of warm Dawn® (a liquid dishwashing detergent sold by The Procter and Gamble Company) in water, methanol, chloroform/methanol, and chloroform to remove the sample from the replica.
11. The replicas are picked up on 300 mesh copper EM grids and examined in a transmission electron microscope.
12. Images are recorded on negative film and positive prints are made from the negatives.
13. The prints are then examined by one of ordinary skill in the art for identification based upon known identification techniques.

The freeze-fracture transmission electron microscopy method is descibed generally in the following references which are incorporated herein by reference: Rash, J. E. and Hudson, C. S., *Freeze-Fracture: Methods, Artifacts, and Interpretations,* New Haven Press, New York, 1979; and Steinbrect and Zierold, *Cryotechniques in Biological Electron Microscopy,* Springer-Verlag, Berlin, 1987. The use of the freeze-fracture transmission electron microscopy method for structure determination and identification is generally described in the following references which are incorporated herein by reference: Gulik-Krzywicki, T., Aggerbeck, L. P. and Larsson, K., "The use of Freeze-Fracture and Freeze-Etching Electron Microscopy for Phase Analysis and Structure Determination of Lipid Systems," *Surfactants in Solution,* K. L. Mittal and B. Lindman, eds., Plenum Press, New York, pp. 237–257, 1984; and Zasadzinski, J. A. N. and Bailey, S. M., "Applications of Freeze-Fracture Replication to Problems in Materials and Colloid Science," J. Elect. Micros. Tech., 13:309–334, 1989.

What is claimed is:

1. A lipstick composition comprising:
   (a) a wax component comprising
      i) from about 3% to about 6% of the composition of candelilla wax;
      ii) from about 2% to about 5% of the composition of ozokerite wax;
      iii) from about 2% to about 5% of the composition of paraffin wax; and
      iv) from about 1% to about 4% of the composition of microcrystalline wax;
   (b) from about 1% to about 90% emollient component comprising one or more oils; and
   (c) a sufficient amount of an oil gelling agent to avoid sweating selected from the group consisting of hydrophobic silica, hydrophobic clays having an effective amount of an activator, propylene carbonate, ethyl cellulose, n-acyl amino acid amides and n-acyl amino acid esters and mixtures thereof,
   wherein said lipstick composition has a rheology defined by a yield value from about 1.5 to about 3.0 grams-force, and a slope m value from about 0.06 to about 0.25 grams-force per second.

2. A lipstick composition according to claim 1 comprising from about 10% to about 80% emollient component comprising from about 5% to about 90% oil.

3. A lipstick composition according to claim 1 wherein said oil is selected from the group consisting of triglycerides, hydrocarbons, silicones, and mixtures thereof.

4. A lipstick composition according to claim 3 wherein said triglyceride is glycerine.

5. A lipstick composition according to claim 1 comprising from about 40% to about 60% emollient component comprising from about 70% to about 90% oil.

6. A lipstick composition according to claim 1 wherein said gelling agent is selected from the group consisting of hydrophobic silica, hydrophobic clay with an effective amount of activator, and mixtures thereof.

7. A lipstick composition according to claim 6 wherein the activator is propylene carbonate and the ratio of clay to activator is about 3:1.

8. A lipstick composition according to claim 7 wherein the gelling agent is a mixture of hydrophobic silica and hydrophobic clay with an effective amount of activator and the activator is propylene carbonate.

9. A lipstick composition comprising:
   (a) a wax component comprising
      i) from about 3% to about 6% of the composition of candelilla wax;
      ii) from about 2% to about 5% of the composition of ozokerite wax;
      iii) from about 2% to about 5% of the composition of paraffin wax; and
      iv) from about 1% to about 4% of the composition of microcrystalline wax;
   (b) from about 1% to about 90% emollient component comprising one or more oils;
   (c) from about 0.1% to about 80% association structure consisting essentially of:
      (1) from about 3% to about 96% polar solvent; and
      (2) from about 4% to about 96% surfactant having a Krafft point at or below about ambient temperature; and
   (d) a sufficient amount of a gelling agent to avoid lipstick sweating selected from the group consisting of hydrophobic silica, hydrophobic clays having an effective amount of an activator, propylene carbonate, ethyl cellulose, n-acyl amino acid amides and mixtures thereof,
   wherein said lipstick composition has a rheology defined by a yield value from about 1.5 to about 3.0 grams-force, and a slope m value from about 0.06 to about 0.25 grams-force per second.

10. A lipstick composition comprising:
    (a) from about 10% to about 30% wax selected from the group consisting of candelilla, beeswax, carnauba, spermaceti, montan, ozokerite, ceresin, paraffin, bayberry, castor waxes and mixtures thereof;
    (b) from about 10% to about 80% of an emollient component comprising from about 5% to about 90%, by weight, oil;
    (c) from about 3% to about 75% of an association structure selected from the group consisting of reverse micelles, lyotropic liquid crystals and mixtures thereof and consisting essentially of:
       (1) from about 5% to about 95% of polar solvent selected from the group consisting of water, glycerine, propylene glycol, panthenol, sorbitol, butylene glycol, and mixtures thereof; and
       (2) from about 5% to about 95% of surfactant having a Krafft point at or below about ambient temperature and selected from the group consisting of amphoteric surfactants, anionic surfactants, cationic surfactants, nonionic surfactants and mixtures thereof;
    (d) from about 1% to about 10% ethyl cellulose; and
    (e) from about 1% to about 20% of a color on an anhydrous pigment weight basis.

11. A lipstick composition according to claim 9 wherein said gelling agent is selected from the group consisting of hydrophobic silica, hydrophobic clay with an effective amount of activator, and mixtures thereof.

12. A lipstick composition according to claim 11 wherein the gelling agent is a mixture of hydrophobic silica and hydrophobic clay with an effective amount of a propylene carbonate activator.

13. A lipstick composition according to claim 11 wherein the ratio of clay to activator is about 3:1.

14. A lipstick composition according to claim 10 wherein said surfactant association structure is selected from the group consisting of cylindrical reverse micelles, reverse hexagonal liquid crystals, lamellar liquid crystals and mixtures thereof.

15. A lipstick composition according to claim 14 wherein said association structure is selected from the group consisting of lamellar liquid crystals, reverse hexagonal liquid crystals and mixtures thereof.

16. A lipstick composition according to claim 15 wherein said lamellar liquid crystals are substantially one phase.

17. A lipstick composition according to claim 16 wherein said reverse micelles aggregate to form networking spherical structures, elongated structures, cylindrical structures, filament structures and mixtures thereof.

18. A lipstick composition according to claim 9 wherein said polar solvent is selected from the group consisting of glycerine, propylene glycol, panthenol, sorbitol, butylene glycol, and mixtures thereof.

19. A lipstick composition according to claim 9 wherein said lipstick composition is substantially free of castor oil.

20. A lipstick composition according to claim 9 wherein said lipstick composition is substantially free of water.

21. A lipstick composition according to claim 9 wherein the oil is selected from oils having solubility parameters which do not differ from each other by more than from about 0.3 to about 1.

* * * * *

UNITED STATES PATENT AND TRADEMARK OFFICE
CERTIFICATE OF CORRECTION

PATENT NO. : 5,843,407
DATED : December 1, 1998
INVENTOR(S) : El-Nokaly, et al

It is certified that error appears in the above-identified patent and that said Letters Patent is hereby corrected as shown below:

In Col. 14, line 45, "Grinsteal" should read --Grindsted--.

In Col. 4, line 65, "alklantoin" should read --allantoin--.

In Col. 2, line 30, "position" should read --positive--.

In Col. 2, line 38, "lechithin" should read --lecithin--.

In Col. 2, line 46, "lechithin" should read --lecithin--.

In Col. 3, line 26, "is used" should read --used is--.

In Col. 3, line 56, "petralatum" should read --petrolatum--.

In Col. 3, line 59, "jojob" should read --jojoba--.

In Col. 3, line 60, "octypalmitate" should read --octylpalmitate--.

In Col. 3, line 60, "soybeam" should read --soybean--.

In Col. 4, line 3, "fro" should read --for--.

In Col. 4, line 4, "lackiness" should read --tackiness--.

In Col. 4, line 17, "trictanoate" should read --trioctanoate--.

In Col. 4, line 17-18, "syntheic" should read --synthetic--.

In Col. 5, line 34, "fro" should read --for--.

In Col. 5, line 38, "the" should read --The--.

In Col. 5, line 53, "nonometers" should read --nanometers--.

In Col. 5, line 55, "nonometers" should read --nanometers--.

In Col. 5, line 66, "(organo0" should read --(organo)--.

In Col. 8, line 12, "Most" should read --More--.

In Col. 8, line 31, "moiturizers/polar" should read --moisturizers/polar--.

In Col. 8, line 34, "surfacant" should read --surfactant--.

UNITED STATES PATENT AND TRADEMARK OFFICE
CERTIFICATE OF CORRECTION

PATENT NO. : 5,843,407
DATED : December 1, 1998
INVENTOR(S) : El-Nokaly, et al

It is certified that error appears in the above-identified patent and that said Letters Patent is hereby corrected as shown below:

In Col. 9, line 24-25, "emulsifying" should read --Emulsifying--.

In Col. 9, line 38, "about" should read --above--.

In Col. 9, line 39, "Drafft" should read --Krafft--.

In Col. 9, line 50-51, "and/jor" should read --and/or--.

In Col. 9, line 67, "termotropic" should read --thermotropic--.

In Col. 10, line 5, "viscualization" should read --visualization--.

In Col. 10, line 17, "are" should read --also--.

In Col. 10, line 21, "work-like" should read --worm-like--.

In Col. 10, line 44, "phase" should read --phases--.

In Col. 10, line 57, "structures," should read --structures--.

In Col. 11, line 25, "surfactans" should read --surfactants--.

In Col. 11, line 27, "use" should read --used--.

In Col. 11, line 44, "e.g." should read --e.g.,--.

In Col. 11, line 46, "e.g." should read --e.g.,--.

In Col. 12, line 2, "monoleate" should read --monooleate--.

In Col. 12, line 9, "amindopropyl" should read --amidopropyl--.

In Col. 12, line 11, "lactate," should read --lactate;--.

In Col. 12, line 24, "betains" should read --betaines--.

In Col. 12, line 26, "propylbetains" should read --propylbetaines--.

In Col. 12, line 28, "acyldicarbody" should read --acyldicarboxy--.

In Col. 12, line 31, "betains" should read --betaines--.

In Col. 12, line 35, "esthers" should read --esters--.

UNITED STATES PATENT AND TRADEMARK OFFICE
CERTIFICATE OF CORRECTION

PATENT NO. : 5,843,407
DATED : December 1, 1998
INVENTOR(S) : El-Nokaly, et al

It is certified that error appears in the above-identified patent and that said Letters Patent is hereby corrected as shown below:

In Col. 12, line 36, "esthers" should read --esters--.

In Col. 12, line 48, "esthers" should read --esters--.

In Col. 12, line 52, "lecithin," should read --lecithin;--.

In Col. 12, line 62, "Cetnrol" should read --Centrol--.

In Col. 13, line 14, "revrse" should read --reverse--.

In Col. 13, line 37, "crystalls" should read --crystals--.

In Col. 13, line 49, "Grace," should read --(Grace,--.

In Col. 13, line 65, "sulfosuccinate," should read --sulfosuccinate;--.

In Col. 13, line 67, "Ltx.)" should read --Ltd.)--.

In Col. 14, line 11, "sulfate," should read --sulfate;--.

In Col. 14, line 11, "sulfate," should read --sulfate;--.

In Col. 14, line 23, "betains" should read --betaines--.

In Col. 14, line 55, "e.g." should read --e.g.,--.

In Col. 15, line 7, "monalaurin" should read --monolaurin--.

In Col. 15, line 17, "Polyoxyethlene" should read --Polyoxyethylene--.

In Col. 15, line 25, "1,8-diol" should read --1,8,diol--.

In Col. 15, line 49, "surfactans" should read --surfactants--.

In Col. 15, line 56, "Cynamid" should read --Cyanimid--.

In Col. 15, line 60, "Generaol" should read --Generol--.

In Col. 15, line 63, "surfactans" should read --surfactants--.

In Col. 16, line 5, "water," should read --water;--.

UNITED STATES PATENT AND TRADEMARK OFFICE
CERTIFICATE OF CORRECTION

PATENT NO. : 5,843,407
DATED : December 1, 1998
INVENTOR(S) : El-Nokaly, et al

It is certified that error appears in the above-identified patent and that said Letters Patent is hereby corrected as shown below:

In Col. 16, line 7, "poloys" should read --polyols--.

In Col. 16, line 24, "preferabty" should read --preferably--.

In Col. 16, line 34, "factors" should read --factors,--.

In Col. 16, line 39, "crystal" should read --crystals--.

In Col. 16, line 57, "one-phse" should read --one-phase--.

In Col. 16, line 60, "by" should read --be--.

In Col. 17, line 21, "structur" should read --structure--.

In Col. 17, line 24, "revers" should read --reverse--.

In Col. 17, line 46, "oil" should read --oils--.

In Col. 17, line 57, "accoarding" should read --according--.

In Col. 19, line 8, "form" should read --from--.

In Col. 19, line 14, "for" should read --from--.

In Col. 19, line 34, "oxide," should read --oxide;--.

In Col. 19, line 35, "oil," should read --oil;--.

In Col. 19, line 37, "salicyclic" should read --salicylic--.

In Col. 19, line 42, "form" should read --from--.

In Col. 19, line 49, "from" should read --form--.

In Col. 21, line 43, "PB-3 Diisosterate" should read --PG-3 Diisostearate--.

In Col. 23, line 5, "Besquare" should read --BeSquare--.

UNITED STATES PATENT AND TRADEMARK OFFICE
CERTIFICATE OF CORRECTION

PATENT NO. : 5,843,407
DATED : December 1, 1998
INVENTOR(S) : El-Nokaly, et al

It is certified that error appears in the above-identified patent and that said Letters Patent is hereby corrected as shown below:

In Col. 25, line 36, "an din" should read --and in--.

In Col. 25, line 65, "FF/TE" should read --FF/TEM--.

In Col. 27, line 67, "thereof," should read --thereof;--.

Signed and Sealed this

Fourth Day of January, 2000

Attest:

Attesting Officer

*Acting Commissioner of Patents and Trademarks*